United States Patent [19]

Rosenberg et al.

[11] Patent Number: 4,857,552
[45] Date of Patent: Aug. 15, 1989

[54] STABLE PHARMACEUTICAL COMPOSITION

[75] Inventors: Leonard S. Rosenberg, Lake Villa; Cheryl Black, Vernon Hills; Earl R. Speicher, Buffalo Grove; Dietmar Wagenknecht, Waukegan, all of Ill.

[73] Assignee: E. I. du Pont de Nemours and Co., Wilmington, Del.

[21] Appl. No.: 203,836

[22] Filed: Jun. 8, 1988

[51] Int. Cl.$^4$ ................... A61K 31/24; A61K 31/195
[52] U.S. Cl. ...................................... 514/538; 514/567
[58] Field of Search ................................. 514/538, 567

[56] References Cited

U.S. PATENT DOCUMENTS 4,454,154 6/1984 Matier ................................. 514/538

Primary Examiner—Frederick E. Waddell
Attorney, Agent, or Firm—Gildo E. Fato

[57] ABSTRACT

An injectable, aqueous pharmaceutical composition for the treatment of cardiac conditions comprising an effective amount of methyl 3-[4-(2-hydroxy-3-isopropylamino)propoxy]phenylpropionate hydrochloride (esmolol) for treating such a cardiac condition, said composition comprising about 1 mg to 250 mg of esmolol per milliliter of said injectable pharmaceutical composition; 0.01 to 0.02M buffer; said composition having a pH range of 4.5 to 5.5, the esmolol degrading in aqueous solution to produce 3-[4-(3-propionic acid)-phenoxy]-1-isopropylamino-2-propanol hydrochloride, said 3-[4-(3-propionic acid)-phenoxyl]-1-isopropylamino-2-propanol hydrochloride having a pK in the pH range of said composition to thereby act as a secondary buffer to increase the buffer capacity and minimize the change in pH as degradation occurs, whereby the stability of esmolol in an aqueous composition is enhanced.

8 Claims, No Drawings

STABLE PHARMACEUTICAL COMPOSITION

BACKGROUND OF THE INVENTION

The present invention relates to pharmaceutical compositions. More particularly, the invention concerns novel compositions in which ester-containing β-blocking drugs are stabilized against hydrolysis during shipping and storage.

In the past, the emphasis in β-blocker research has been to develop stable drugs which could be administered to cardiac patients over relatively long periods of time. However, it is often desirable in the critical care setting to quickly reduce heart work or improve rhythmicity during a cardiac crisis, e.g., during or shortly after a myocardial infarction. Conventional β-blocking agents can be employed for such treatment, but their long durations of action can cause undesirable side effects.

Recently, certain compounds containing ester functions have been found to possess β-adrenergic blocking activity. (See U.S. Pat. No. 4,387,103 to Erhardt, et al., June 7, 1983, and U.S. Pat. No. 4,593,119, June 3, 1986.) These compounds generally have a short duration of action in vivo, and do not possess the disadvantages of the conventional β-blockers described above. The ester groups in these compounds have, however, been found to be somewhat unstable in aqueous environments, such as intravenous infusion solutions. The practical effect of this instability is that conventional compositions containing the compounds have relatively short shelf lives, thus making commercial distribution and storage difficult.

Therefore, there remains a need for pharmaceutical preparations of short-acting β-blockers which are stable in vitro and have a relatively long storage life.

SUMMARY OF THE INVENTION

In accordance with the present invention, disclosed herein is an aqueous pharmaceutical composition for the treatment or prophylaxis of cardiac disorders in a mammal comprising from about 1 mg to about 250 mg/mL of injectable pharmaceutical composition of a β-adrenergic blocking compound having the formula:

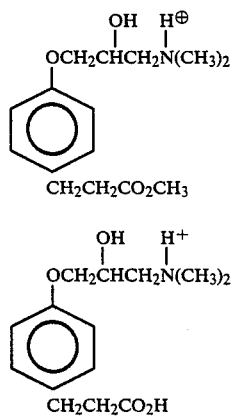

or a pharmaceutically acceptable salt thereof, said compound (esmolol) degrading in aqueous solution to produce 3-[4-(3-propionic acid)-phenoxy]-1-isopropylamino-2-propanol (degradation product), said degradation product having a pK in the pH range of the composition to thereby act as a secondary buffer to increase the buffer capacity and minimize the change in pH and thereby maximize the stability of esmolol in an aqueous composition.

DETAILED DESCRIPTION OF THE INVENTION

In accordance with the present invention, it has been discovered that a stable pharmaceutical composition possessing a relatively long shelf life can be prepared using a short-acting, ester-containing β-blocker of the formula:

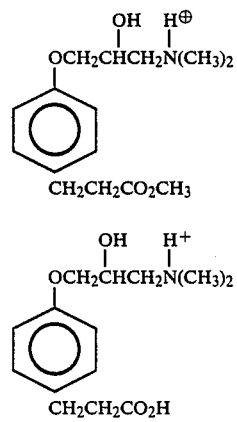

or a pharmaceutically acceptable salt thereof, preferably the hydrochloride salt.

The stability of methyl 3-[4-(2-hydroxy-2-isopropylamino)propoxy]phenylpropionate (esmolol) in water is mediated by the rate of acid/base hydrolysis of the labile aliphatic methyl ester group. Current esmolol formulations use alcohol and propylene glycol to minimize the concentration of water in the formulation and, therefore, slow this degradation pathway. As an alternative to the mixed organic/aqueous formulation, work has been done in totally aqueous solutions. This work has shown that the rate of degradation of esmolol can be reduced by:

(1) use of acetate as the buffer,
(2) maintaining the pH as near to pH=5.0 as possible,
(3) minimizing the concentration of esmolol in solution, and
(4) minimizing the concentration of buffer used.

If these four conditions can be met, then it is possible to formulate esmolol in a totally aqueous solution with an acceptable shelf life.

Each of the four conditions necessary for a stable aqueous esmolol solution, as outlined above, are discussed hereinafter. As is apparent, the shelf life of an aqueous esmolol formulation can be maximized by the correct choice of buffer, pH and esmolol concentration. The novel use of a 'secondary buffer' to minimize the buffer concentration is critical to the stability of the aqueous formulation.

Buffers tested for their effect on the stability of esmolol were: acetate, tartrate, lactate, gluconate, sodium phosphate, and 3-[4-(3-propionic acid)-phenoxy]-1-isopropylamino-2-propanol (degradation product). From these experiments, acetate buffer provided the best esmolol stability in aqueous solution. As such, it was chosen as the formulation buffer.

The stability of esmolol in water has been determined from pH=0 to pH=12. The pH showing maximum stablity was found to be pH=5.0±0.50. A pH stability profile in acetate buffer was run from pH=4 to pH=7. Maximum stability was found to be in a narrow pH range centered around pH=5.0. The breadth of this stability appears to be very narrow (i.e. ±0.2 pH units).

The rate of degradation of esmolol has been shown to decrease as the concentration of esmolol decreases. The preferred aqueous formulation described is 1% (10 mg/mL) versus a 25% (250 mg/mL) glycol/alcohol based solution of esmolol.

The choice of acetate as the buffer, the reduction in the concentration of esmolol in solution, and the maintenance of the pH in a narrow range around pH=5 all favor a stability enhancement for esmolol in a totally aqueous media. The fourth condition necessary for an acceptably stables esmolol aqueous formulation is the reduction in the concentration of acetate buffer. In the absence of a 'secondary buffering' affect, a higher than desired concentration of acetate would be required to maintain the optimum pH.

The concentration of acetate buffer necessary in solution can be reduced to acceptable levels due to the nature of the degradation of esmolol in solution. This is because:

(1) esmolol degrades to the degradation product in solution;

(2) the degradation product has a pK of 4.80; and (3) this pK is in the pH range of the formulation.

Thus, as esmolol degrades in aqueous solution it 'produces' a secondary buffer which is active (i.e. has an additive effect on the buffer capacity of the formulation) in the pH range of the formulation. The equations, and their derivations, necessary to calculate the change in pH due to degradation in the presence of a secondary buffer are described hereinafter. By calculating the projected pH changes expected for the 1% formulation, it has been possible to minimize the amount of primary buffer (acetate) used in the formulation.

Described is the identification, calculation and use of a degradation product as a secondary buffer to stabilize a formulation. The advantages of this secondary buffering system are:

(1) the secondary buffer is produced due to degradation and, therefore, the buffer capacity increases as degradation occurs;

(2) the concentration of primary buffer in the formulation can be minimized, thereby enhancing the stability of esmolol in a totally aqueous formulation. The majority of the buffering capacity of the formulation is due to the secondary buffer being produced, and not due to the primary acetate buffer. This is enhanced since, (3) the pK of the secondary buffer, the degradation product, is just below the initial pH (i.e. the pH of maximum stability).

This maximizes the buffer capacity of the secondary buffer and reduces the change in pH due to degradation. The stability and shelf life of esmolol in an aqueous formulation is thereby increased. Another advantage of the totally aqueous formulation is that there are no 'extra' routes of degradation possible. The only possible competing reaction, in the totally aqueous formulation of esmolol, is the recombination of the degradation product and methanol to reform esmolol.

The pH of a parenteral pharmaceutical product is normally set at an optimal value for stability, solubility and other formulation factors. With time, most drugs will begin to degrade in solution. This degradation can cause a change in the pH of the solution, due to the production or consumption of acid or base. An accurate prediction of the change in pH is useful in formulating a drug, as well as predicting the shelf life expectancy of the formulation.

An accurate prediction of the change in pH due to degradation is a straightforward problem when the degradation product(s) do not interfere with the calculations. In these cases a simple Henderson-Hasselbalch equation can be used to predict the change in the pH of the solution. However, if the degradation creates a compound with an ionizable group (secondary buffer), then the prediction of the pH change, by calculation, may need to include and correct for this. In order to perform these calculations it is necessary to know the type of ionizable group (acidic or basic) created by the degradation, and the protonation state of this group immediately subsequent to its formation. The type of group (acid or base), protonation state, and the pH of the solution will then determine whether a hydronium or hydroxide ion is donated to, or consumed from, the solvent by the secondary buffer. The three possible cases are:

(1) the pK of the secondary buffer is much greater than the pH of the solution;

(2) the pK of the secondary buffer is much lower than the pH of the solution; and (3) the pK of the secondary buffer is comparable to the pH of the solution.

Presented are equations to accurately calculate the pH change for the degradation of esmolol (i.e. the degradation product acts as a secondary buffer, case 3).

Esmolol degrades by a water mediated hydrolysis of its aliphatic carboxy methyl ester, to the degradation product noted and methanol. The resulting degradation product as a pK of 4.80 which is within the pH range (formulation pH ±1.0) of the desired formulation. This secondary buffer (degradation product) affects the change in the pH due to its ability to act as a buffer. Equations to correct the calculated pH, due to this secondary buffering effect, are presented. The equations presented accurately predict the pH change due to degradation when the secondary buffer is an acid. Derivation of equations to correct for the secondary buffering of a basic compound can be made from the equations presented.

The pK for the aliphatic amino group of esmolol was determined by a differential potentiometric method. This method has been extensively described (L. S. Rosenberg, et al., Drug Development and Industrial Pharmacy, 12(10), 1449–1467, (1986). The pK for the aliphatic carboxy group of the degradation product of esmolol was determined by a routine potentiometric titration method, using the same method as described previously. Both pKs were determined in aqueous solution.

The degradation kinetics of esmolol were determined by monitoring the loss of esmolol by an HPLC routine. The HPLC procedure use a 15 cm, uBondapak Cyano column (Waters) and a Hitachi 655-11A pump with a Hitachi 655A variable wavelength UV detector set at 214 nm. The mobile phase was acetonitrile:0.1 M sodium acetate:glacial acetic acid; 15:84:1, at a 1 mL/min flow rate. Samples were diluted into 3 mL of milli-Q water to quench the degradation and then kept at room temperature until they were analyzed. The rate of degradation at room temperature is minimal, and the samples were assayed within a week of sampling.

The change in pH due to degradation was determined using an ION 85 Radiometer with a semi-micro Ross electrode. All samples were allowed to cool to room temperature before the pH was measured.

Routinely in the development of a parenteral product a number of buffer systems are investigated to assess their relative affects on the stability of the formulation. If the change in the pH due to degradation is known, apriori, then the concentration of buffer necessary for optimal pH maintenance can be predicted. This can reduce the number of formulation screens necessary to optimize a drug's formulation.

The change in pH, due to degradation, of an aqueous formulation using an acetic acid/acetate buffer can be calculated by the Henderson-Hasselbalch equation:

$$[H^+] = K_a * \frac{[HA]_o + C_d}{[A^-]_o - C_d} \quad (1)$$

where $$[HA]_o = \frac{[H^+]_o * C_t}{[H^+]_o + K_a} \quad (2)$$

and $$[A^-]_o = \frac{K_a * C_t}{[H^+]_o + K_a} \quad (3)$$

where $[HA]_o$ and $[A^-]_o$ are the relative concentrations of acetic acid and acetate, respectively. $[H^+]_o$ is the hydrogen ion concentration at the initial pH, $K_a$ is the ionization constant of the buffer, and $C_t$ is the total initial concentration of the buffer. $[H^+]$ is the hydrogen ion concentration at any amount of degradation and $C_d$ is the molar concentration of base consumed or acid produced, due to the hydrolysis of esmolol. Equation 1 can be used to predict the change in the pH of a formulation for any percent drug loss.

Assuming that the result of hydrolysis is to produce a product which has a pK in the pH range of the formulation, then equation 1 is modified to account for the increased buffer capacity of the secondary buffer by:

$$[H^+] = K_a * \frac{[HA] + C_d - [DH]}{[A^-] - C_d + [DH]} \quad (4)$$

where [DH] is the concentration of secondary buffer produced due to degradation. Assuming that one mole of this secondary buffer is produced per mole of drug degraded, then the concentration of secondary buffer can be calculated by:

$$[DH] = \frac{[H^+] * C_d}{[H^+] + K_d} \quad (5)$$

where $[H^+]$ is the hydrogen ion concentration at the calculated pH and $K_d$ is the ionization constant of the secondary buffer. Combining equation 4 and 5 and rearranging gives:

$$[H^+]^2[A^-]_o + [H^+]*(K_d[A^-]_o - C_d K_d - [HA]_o K_a) - K_a K_d * ([HA]_o + C_d) = 0 \quad (6)$$

Equation 6 can be solved by the quadratic equation for any initial pH and concentration of buffer to give the pH for any percent degradation.

In equation 4, the concentration of secondary buffer produced mediates the decrease in pH by its ability to consume acid produced by the hydrolysis of esmolol.

Many times the active drug, or the excipients, do not degrade in such a fashion that the products have an ionizable group(s). In these cases, the only buffering capacity of the formulation will be that of the primary buffer. The concentration of primary buffer will have to be large enough to prevent significant pH changes. The amount of buffer necessary will vary according to the drug, pH-stability requirements, ionic strength effects, and other formulation factors. The change in the initial formulation pH, due to degradation, can be accurate predicted by equation 1.

If the rseult of degradation is to create a product with an acidic ionizable group, which has a pK more than 2 pH units higher than the pH of the formulation, then the pH of the solution will not change due to degradation. This assumes that the degradation reaction consumes one mole of base (produces one mole of acid) and produces one mole of secondary buffer for each mole of drug lost. Then the secondary buffer will consume one mole of acid to protonate the 'created' conjugate base for each mole of degraded active drug substance. This is the 'best case' possible. The pH will not change due to hydrolysis of the esmolol and, therefore, the concentration of primary buffer necessary can be minimized.

Previous experiments have shown that esmolol degrades by hydrolysis of its aliphatic methyl ester consuming one mole of hydroxyl ions for each mole of esmolol degraded. The degradation product and one mole of methanol are the only degradation products. This degradation pathway results in the net production of one mole of acid for each mole of esmolol degraded. The secondary buffer is 'produced' in its conjugate base form. The degradation product increases the buffer capacity of the formulation as it is formed, thereby minimizing the change in pH due to degradation. Thus, the buffer capacity of the formulation increases as the amount of degradation increases. This allows the primary buffer concentration to be reduced initially and set according to stability, isotonicity and other formulation factors.

The stability of esmolol in aqueous solution is affected by several formulation factors. First, the optimal pH for stability, in acetate buffer, is found to be in a narrow range centered around pH=5.0. Secondly, the concentration of acetate buffer affects the stability of esmolol in solution. Experiments have shown that the rate of hydrolysis of esmolol is dependent on the concentration of acetate buffer. As the concentration of acetate is increased, the rate of hydrolysis of esmolol also increases.

In the formulation of many parenteral compounds this sort of dictomy exists. The need to increase one component of the formulation for stability, in fact, compromises the product's shelf life due to other competing solution factors. However, it has been found that if the problem is pH versus buffer capacity and the drug degrades to produce a secondary buffer, then this formulation problem can be circumvented.

The actual change in the pH due to degradation of esmolol is shown in Table I. For comparison purposes, the calculated change in pH with and without correction for a secondary buffer is also listed. For the 50 mg/mL (5%) formulation, the change in the uncorrected pH (no secondary buffering affect) is rapid for the 0.01 M buffer. By 20% esmolol degradation, this pH is less than 2. For the 0.05 M buffer, the buffer capacity is completely compromised by 20% degradation and its pH is less than 3. At 0.10 M buffer concentration, the pH does not decrease as dramatically, however, the pH is not maintained within 0.5 pH units of the initial pH. Therefore, in the absence of a secondary buffering affect, more than 0.10 M acetate buffer would be necessary initially.

In the presence of a secondary buffering affect, the pH of the 50 mg/mL formulation is maintained within 0.5 pH units of the initial pH of the 0.05 M acetate buffer. Even for 0.01 M acetate buffer, the formulations buffer capacity is not completely neutralized by 20% degradation. Therefore, the concentration of acetate buffer necessary for pH maintenance over the shelf life of this product can be reduced by more than a factor of two by the formation of a secondary buffer.

For the 100 mg/mL (10%) formulation of esmolol, the change in pH due to degradation in the absence of a secondary buffering affect is dramatic. At even 0.10 M acetate buffer, the pH decreases to less than 2.5 for 20% degradation. Substantially more than 0.10 M acetate buffer would be required to maintain the pH within optimal limits. However, due to the presence of a secondary buffering affect, the concentration of primary buffer can be set at 0.10 M.

FIG. 1

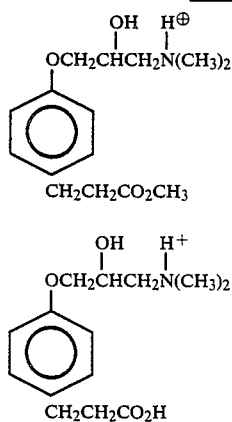

TABLE I

Predicted versus Actual Change in the Formulation pH Due to Degradation
pH initial is pH = 5.0

| Acetate Buffer | Esmolol (mg/mL) | Percent De-graded | Un-corrected* pH | Corrected+ pH | Actual pH |
|---|---|---|---|---|---|
| 0.01 M | 50 | 5 | 2.68 | 4.48 | 4.56 |
| | | 10 | 1.98 | 4.26 | 4.21 |
| | | 15 | 1.72 | 4.11 | 4.05 |
| | | 20 | 1.56 | 4.00 | — |
| | 100 | 5 | 1.98 | 4.26 | 4.33 |
| | | 10 | 1.56 | 4.00 | 4.02 |
| | | 15 | 1.35 | 3.84 | 3.75 |
| | | 20 | 1.21 | 3.73 | 3.63 |
| 0.05 M | 50 | 5 | 4.70 | 4.83 | 4.86 |
| | | 10 | 4.38 | 4.72 | 4.67 |
| | | 15 | 3.93 | 4.62 | 4.59 |
| | | 20 | 2.72 | 4.55 | — |
| | 100 | 5 | 4.38 | 4.72 | 4.79 |
| | | 10 | 2.72 | 4.55 | 4.47 |
| | | 15 | 1.73 | 4.43 | 4.35 |

TABLE I-continued

Predicted versus Actual Change in the Formulation pH Due to Degradation
pH initial is pH = 5.0

| Acetate Buffer | Esmolol (mg/mL) | Percent De-graded | Un-corrected* pH | Corrected+ pH | Actual pH |
|---|---|---|---|---|---|
| | | 20 | 1.45 | 4.33 | — |
| 0.10 M | 50 | 5 | 4.85 | 4.91 | 4.90 |
| | | 10 | 4.70 | 4.83 | 4.83 |
| | | 15 | 4.55 | 4.77 | 4.73 |
| | | 20 | 4.38 | 4.72 | 4.69 |
| | 100 | 5 | 4.70 | 4.83 | 4.85 |
| | | 10 | 4.38 | 4.72 | 4.72 |
| | | 15 | 3.93 | 4.58 | 4.58 |
| | | 20 | 2.42 | 4.52 | 4.52 |

*Equation 1
+Equation 4

TABLE II

Predicted versus Actual Change in the Formulation pH Due to Degradation
pH initial is pH = 5.5
Acetate buffer concentration is 0.05 molar

| Esmolol Concentration (mg/mL) | Percent Degraded | Uncorrected* pH | Corrected+ pH | Actual pH |
|---|---|---|---|---|
| 10 | 5 | 5.39 | 5.41 | 5.40 |
| | 10 | 5.30 | 5.34 | 5.33 |
| | 15 | 5.21 | 5.27 | 5.25 |
| | 20 | 5.13 | 5.22 | — |
| 50 | 5 | 5.06 | 5.17 | 5.15 |
| | 10 | 4.74 | 4.99 | 4.95 |
| | 15 | 4.42 | 4.86 | — |
| | 20 | 3.96 | 4.76 | — |

*Equation 1
+Equation 4

EXAMPLE 1

The following describes the preparation of vials of a pharmaceutical composition of the present invention containing 10 mL of solution with a concentration of esmolol HCl of 10 mg/mL. The concentration of each ingredient of the composition, in an amount per mL solution, was as follows:

| | Amount/mL Solution |
|---|---|
| Esmolol HCl | 10 mg |
| Sodium Acetate · 3H$_2$O | 2.8 mg |
| Glacial Acetic Acid USP | 0.546 mg |
| Sodium Hydroxide Solution (10N) | pH adjusted to 5.0 |
| Hydrochloric Acid Solution (5N) | pH adjusted to 5.0 |
| Water for Injection USP | qs |

The vials and glassware for compounding, filtering and filling were washed and depyrogenated. The filter assembly, filling tube assembly, and other parts and equipment were sterilized.

Seventy-six percent of the final volume of cool water for injection was collected in a compounding tank. The sodium acetate was added and the solution was stirred until the sodium acetate dissolved. The glacial acetic acid was then added and the solution was stirred for 5 minutes after which the esmolol HCl was added and stirring was continued until all of the ingredients were dissolved. The pH of the solution is then adjusted to 4.9 to 5.1 using hydrochloric acid or sodium hydroxide. The solution is then brought to final volume with cool water for injection, 25° C.±5° C. and the pH is adjusted to 4.9 to 5.1 if necessary. The solution was then placed in vials which were sealed, leak tested and inspected.

EXAMPLE 2

Vials prepared according to the procedure of Example 1 were selected and placed on stability test. At each stability time one ampul of each solution was removed. The pH, potency and the physical appearance of the solutions were determined. The concentration of the drug was determined by a high performance liquid chromatographic (HPLC) method. Each vial contained 10 mL of solution and was stored in the inverted position which is an aggressive test because of the solution to stopper contact. The results are tabulated in Table III.

The glossary for the abbreviations used in the table is as follows:
TZ—Initial, zero time
RT—Room temperature, 15° to 30° C.
EL40—40° C.
EL55—55° C.
EL75—75° C.
MOS—Months Samples were dissolved or diluted with the mobile phase, methanol—pH 3.4 phosphate buffer solution. The resulting solutions were diluted with benzoic acid internal standard solution and chromatographed on a octadecyl silane column with detection at 229 nm. The selectivity of the chromatographic system for intact compound was demonstrated by resolving the parent drug from synthetic intermediates, potential impurities and reaction products resulting from accelerated degradation conditions. The method is linear, quantitative, rugged and reproducible with a sensitivity of 2 μg/mL.

Either peak height or peak area ratios can be used for quantitation.

esmolol/mL of solution; 0.01 to 0.04 M buffer; said composition having a pH range of about 4.5 to 5.5, the esmolol degrading in aqueous solution to produce 3-[4-(3-propionic acid)-phenoxy]-1-isopropylamino-2-propanol hydrochloride, said 3-[4-(3-propionic acid)-phenoxy]-1-isopropylamino-2-propanol hydrochloride having a pK in the pH range of said composition to thereby act as a secondary buffer to increase the buffer capacity without the addition of buffer and minimize the change in pH as degradation occurs, whereby the stability of esmolol in an aqueous composition is enhanced.

2. The composition of claim 1 wherein the buffer is selected from the group comprising acetate, tartrate, lactate, gluconate and phosphate buffer.

3. The composition of claim 2 wherein the buffer is acetate buffer.

4. The composition of claim 3 including about 10 mg/mL of solution.

5. The composition of claim 4 wherein the concentration of acetate buffer is about 0.05 M.

6. The composition of claim 5 wherein a pH of about 4.9 to about 5.1.

7. A stable, injectable, aqueous pharmaceutical composition for the treatment of cardiac conditions comprising an effective amount of Methyl 3-[4-(2-hydroxy-3-isopropylamino)propoxy]phenylpropionate hydrochloride (esmolol) for treating such a cardiac condition, said composition comprising about 10 mg of esmolol/mL of solution; about 0.05 M buffer; said composition having a pH range of about 4.5 to 5.5, the esmolol degrading in aqueous solution to produce 3-[4-(3-propionic acid)-phenoxy]-1-isopropylamino-2-propanol hydrochloride, said 3-[4-(3-propionic acid)-phenoxy]-1-isopropylamino-2-propanol hydrochloride having a pK in the pH range of said composition to thereby act as a

TABLE III

Stability of the Formulation at Various Temperatures and Times

| Test Time | Potency (Active) Value | Potency (Active) Change (%) | pH Value | pH Change (pH) | Physical Observations |
|---|---|---|---|---|---|
| ALL TZ | 110.0 | 0.0 | 5.04 | 0.0 | CLEAR COLORLESS SOLUTION |
| EL40 | | | | | |
| 1 mos | 105.8 | −4.2 | 5.01 | −0.0 | CLEAR COLORLESS SOLUTION |
| 2 mos | 106.0 | −4.0 | 5.00 | −0.0 | CLEAR COLORLESS SOLUTION |
| 3 mos | 101.7 | −8.3 | 4.96 | −0.1 | CLEAR COLORLESS SOLUTION |
| 6 mos | 101.0 | −9.0 | 4.93 | −0.1 | CLEAR COLORLESS SOLUTION |
| EL55 | | | | | |
| 1 mos | 102.5 | −7.5 | 4.91 | −0.1 | CLEAR COLORLESS SOLUTION |
| 2 mos | 100.9 | −9.1 | 4.90 | −0.1 | CLEAR COLORLESS SOLUTION |
| 3 mos | 90.3 | −19.7 | 4.81 | −0.2 | CLEAR COLORLESS SOLUTION |
| EL75 | | | | | |
| 1 mos | 74.3 | −35.7 | 4.65 | −0.4 | CLEAR COLORLESS SOLUTION |
| 2 mos | 56.0 | −54.0 | 4.51 | −0.5 | CLEAR COLORLESS SOLUTION |
| RT | | | | | |
| 1 mos | 107.8 | −2.2 | 5.03 | −0.0 | CLEAR COLORLESS SOLUTION |
| 2 mos | 109.5 | −0.5 | 5.03 | −0.0 | CLEAR COLORLESS SOLUTION |
| 3 mos | 106.6 | −3.4 | 5.03 | −0.0 | CLEAR COLORLESS SOLUTION |
| 6 mos | 107.3 | −2.7 | 5.04 | 0.0 | CLEAR COLORLESS SOLUTION |
| 9 mos | 109.1 | −0.9 | 5.02 | −0.0 | CLEAR COLORLESS SOLUTION |

What is claimed is:

1. An injectable, aqueous pharmaceutical composition for the treatment of cardiac conditions comprising an effective amount of Methyl 3-[4-(2-hydroxy-3-isopropylamino)propoxy]phenylpropionate hydrochloride (esmolol) for treating such a cardiac condition, said composition comprising about 1 mg to about 250 mg of secondary buffer to increase the buffer capacity without the addition of buffer and minimize the change in pH as degradation occurs, whereby the stability of esmolol in an aqueous composition is enhanced.

8. The composition of claim 7 having a pH of about 4.9 to about 5.1.

* * * * *